(12) United States Patent
Schutt

(10) Patent No.: US 6,365,167 B1
(45) Date of Patent: Apr. 2, 2002

(54) REACTION PRODUCT OF ARGININE AND P-AMINOBENZOIC ACID, COSMETIC, AND HUMAN AND ANIMAL HEALTH COMPOSITIONS THEREOF

(75) Inventor: Steven R. Schutt, Teaneck, NJ (US)

(73) Assignee: Epicare Ltd., Prescott, AZ (US)

( * ) Notice: Subject to any disclaimer, the term of this patent is extended or adjusted under 35 U.S.C. 154(b) by 0 days.

(21) Appl. No.: 09/020,284

(22) Filed: Feb. 6, 1998

Related U.S. Application Data

(63) Continuation of application No. 08/532,331, filed on Sep. 22, 1995, now Pat. No. 5,734,080.

(51) Int. Cl.[7] .............................. A61K 6/00; A61K 7/00; A61K 31/74
(52) U.S. Cl. ..................................... 424/401; 424/78.06
(58) Field of Search .............................. 424/78.06, 401, 424/70.1, 60

(56) References Cited

U.S. PATENT DOCUMENTS 5,734,080 A * 3/1998 Schutt ........................ 562/553

* cited by examiner

*Primary Examiner*—Thurman K. Page
*Assistant Examiner*—S. Howard
(74) *Attorney, Agent, or Firm*—Walter Katz

(57) ABSTRACT

What is described herein is the reaction product of arginine and p-aminobenzoic acid (PABA), cosmetic and human and animal health compositions thereof, useful for treating wounds (small or large animals and humans), burns (small or large animals and humans), sunburn (in humans, dogs and sheep), non-specific vaginitis (large animals), dermatitis (small or large animals and humans), pyoderma (small and large animals), rhabditis dermatitis (dogs and cattle), eczema nasi (dogs), exudative epidermitis (swine), saddle sores (horses), proudflesh (horses), hutchburn (rabbits), dermal lesions (small or large animals and humans), udder edema (cattle, goats and sheep), abscesses (small or large animals and humans) and bovine mastitis.

6 Claims, No Drawings

REACTION PRODUCT OF ARGININE AND P-AMINOBENZOIC ACID, COSMETIC, AND HUMAN AND ANIMAL HEALTH COMPOSITIONS THEREOF

This application is a con't of Ser. No. 08/532,231 filed Sep. 22, 1995, U.S. Pat. No. 5,734,080.

BACKGROUND OF THE INVENTION

1. Field of the Invention

This invention relates to cosmetic and human and animal health compositions, and, more particularly, to the reaction product of arginine and p-aminobenzoic acid (PABA), and compositions thereof, useful for treating wounds, lesions, burns, sunburn, the hair and scalp, hemorrhoids and teeth, in animals and humans, including bovine mastitis.

2. Description of the Prior Art

The prior art does not disclose the reaction product of arginine and p-aminobenzoic acid (PABA), and cosmetic and health compositions and formulations thereof. For example, U.S. Pat. No. 4,499,067 discloses only acyl arginine derivatives without PABA; U.S. Pat. No. 4,921,939 discloses only forming guanidine sweetening agents by reaction of substituted arcyl amines with guanidino moieties; U.S. Pat. No. 5,110,797 discloses peptide substituted/reacted arginine, however, without PABA; and U.S. Pat. No. 5,298,647 discloses PABA/amino acid reaction products which may be used as ultraviolet protecting agents, but arginine is not disclosed.

SUMMARY OF THE INVENTION

What is described herein is the reaction product of arginine and p-aminobenzoic acid, compositions thereof, and its use in treating or preventing wounds, lesions, burns, sunburn, the hair and scalp, hemorrhoids, and teeth, in animal and humans including, bovine mastitis.

DETAILED DESCRIPTION OF THE INVENTION

The composition of the invention comprises the formulation given in Table 1 below:

TABLE 1

Composition of Invention

| | Percent by Wt. | | |
|---|---|---|---|
| Component | Suitable | Preferred | Optimum |
| Reaction product of arginine and p-aminobenzoic acid (PABA) (as a powder, aqueous solution, gel or emulsion for example) | 0.5–10 | 1–5 | 2.29 |
| Biotin | 0–0.05 | 0.01–0.2 | 0.0066 |
| Calcium Pantothenate | 0–5 | 0.1–0.5 | 0.33 |
| Myoinositol | 0–1.0 | 0.1–0.5 | 0.33 |

The reaction product of arginine and PABA is prepared as follows:

EXAMPLE 1

Reaction Product of Arginine and p-Aminobenzoic Acid

A solution of 10 g of p-aminobenzoic acid, 99% (Fluka-SAF 06940) was prepared by dissolving the acid in 50 ml isopropanol (Fluka-SAF 59310) at 60° C. with agitation. Then a slurry of 10 g of 1-arginine, 98% free base (Fluka-SAF 11010) in 50 ml of isopropanol at 60° C. was added to the solution. The reaction product was filtered to yield 14 g of the reaction product, referred to hereinafter as arginine aminobenzoate.

A typical composition of the invention was prepared as follows:

EXAMPLE 2

A typical composition of the invention had the following active and inert ingredients therein.

TABLE 2

| | Percent by Wt. |
|---|---|
| ACTIVE INGREDIENTS | |
| Reaction Product of Example 1 | 2.29 |
| d-Calcium Pantothenate | 0.33 |
| myo-Inositol | 0.33 |
| d-Biotin | 0.0066 |
| Thymine | 0.000016 |
| Guanine | 0.000016 |
| Cytosine | 0.000016 |
| Adenine | 0.000016 |
| | 2.96% |
| INERT INGREDIENTS AND PRESERVATIVES | |
| Deionized H$_2$O | 70.57% |
| Mixed oils | |
| Safflow oil (or equiv) | 7.53 |
| Persic oil | 3.38 |
| Tocopherol | 1.17 |
| Borage oil | 0.72 |
| Coconut oil | 0.72 |
| Tea tree oil | 0.69 |
| Lanolin | 0.36 |
| Lecithin | 0.22 |
| | 14.79 |
| Glycerine | 10.24 |
| Carbopol 980 | 0.65 |
| Tween 80 | 0.41 |
| Aloe Vera (freeze dried) | 0.33 |
| Camphor (natural) | 0.27 |
| Methyl paraben | 0.25 |
| Zinc peroxide | 0.25 |
| Pemulin TR1 | 0.16 |
| Propyl paraben | 0.1 |
| Ethyl paraben | 0.05 |
| Silver benzoate | 0.025 |
| Butylated hydroxytoluene | 0.01 |
| | 100.00% |

A cream formulation was prepared as follows:

EXAMPLE 3

Cream Formulation

Base (C)
to 50 ml glycerin
add with low shear agitation
500 mg methyl paraben and
150 ml deionized water,
continue agitation and add
2 g freeze dried aloe (Triarco),
2 g d-calcium pantothenate (Eastman),
2 g myo-inositol (Fluka-SAF 57576),
250 mg ethyl paraben, 400 mg propyl paraben,
100 mg silver benzoate,
40 mg (+) biotin (Fluka-SAF 14400),
100 mcg thymine 99% (Fluka-SAF 89310),
100 mcg guanine (Fluka-SAF 51010),
100 mcg cytosine (Fluka-SAF 30430), and
100 mcg adenine (Fluka-SAF 01830).
Cream When all the dry ingredients are present in solution, add with low shear agitation
200 ml 2% mucilage Carbopol 980,
continue agitation, and add
part A-1 consisting of
100 ml part A
2.5 ml Tween 80
500 mg methyl paraben
1 g Pemulin TR1
added and dissolved at low shear. Then, the resulting emulsion (parts A-1 & C) was neutralized with 14 grams of arginine aminobenzoate in 30 ml deionized water, to provide a cream with a pH of 5.5. Then adjust the pH to 7.7 with 10 ml of 2.5N (10%) NaOH.

EXAMPLE 4

Mast Aid Intermammary

Add 1.25 grams zinc peroxide to the cream formulation of Example 3.

Mechanism of Action of Composition of Invention

The composition of the invention in human and animal health care is referred to herein as the effective action of "Cell Differentiation Regulatory Mechanism Response Enabling Composition" (CDRMREC). In such response, the composition of arginine-PABA affects the regulatory mechanism that governs the process of cell division. When applied topically, the CDRMREC causes activation of the proliferative phase in the DNA regulatory mechanism which speeds the rate of cellular response in the process, for example, of wound healing. Additionally, the composition herein can accelerate the micro-circulation which affects the process of inflammation control at the site of injury. The stimulation of micro-circulation by CDRMREC focuses the body's increased humoral response to trauma at the site of injury. This increase in the natural micro-circulation also provides ancillary benefits such as the debridement of necrotic tissue, removal of edema, and support of accelerated cell repair. CDRMREC also affects the chemistry surrounding the micro-neuron receptors within damaged cells, thus controlling spontaneous pain at the actual site of injury without diminution of other sensations.

When treated with the composition of the invention, lesions such as burns, ulcers, wounds, lacerations, and damaged, as well as normal skin, are observed to show the following responses:

1. Treated lesions show accelerated epithelialization.
2. Treated lesions show accelerated endothelialization.
3. Treated lesions show accelerated mesothelialization.
4. Treated lesions had a lack of scab formation.
5. Treated lesions rapidly form rolled edges.
6. Treated skin lacerations close in less than 4 hours.
7. Treated lacerations stop bleeding in less than 3 minutes.
8. Treated lesions such as burns, ulcers, wounds and lacerations show selective abatement of spontaneous pain without diminution of other sensation in the affected area.
9. Treated lesions epithelialize into pink unpigmented translucent skin.
10. All treated lesions show suppression or absence of cicatrixization.

The composition of the invention has proven effective in the treatment or prevention of human and animal health problems as described below.

In topical form, CDRMREC has treated:
Wounds (small or large animals and humans).
Burns (small or large animals and humans).
Sunburn (in humans or sheep and dogs after shearing).
Non-specific vaginitis (large animals).
Dermatitis (small or large animals and humans).
Pyoderma (small or large animals and humans).
Rhabditic dermatitis (dogs and cattle).
Eczema Nasi of dogs.
Exudative epidermitis (pigs).
Pityriasis rosea (pigs).
Saddle Sores (horses).
Hutchburn (rabbits).
Dermal lesions (small or large animals and humans).
Udder edema (cattle, goats and sheep).
Abscesses (small or large animals and humans).
BURNS An excellent sunscreen with an SPF of 15 or better, CDRMREC reduced the pain and removed the redness of sunburn very rapidly. It moisturized dry and sunburned skin while promoting and prolonging a tan. CDRMREC also prevented blistering and peeling.

During the clinical test of CDRMREC by artificially induced sunburn, the treated site changed color from red to brown almost immediately upon application. All erythema had disappeared within the first hour of treatment. The pain at the CDRMREC treated site also disappeared in less than 5 minutes. The treated site did not peel and maintained its tan for a month after the control site had faded.

CDRMREC has reduced the pain and alleviated redness associated with burns (1st and 2nd degree). It moisturized burned skin (1st and 2nd degree) and rapidly facilitated healing of burns (1st, 2nd and 3rd degree) while preventing or suppressing blistering. When treating 3rd degree burns there was accelerated epithelialization and diminution of scarring without formation of keloid tissue.

CDRMREC has successfully treated frost bite and wind burn.

Surface Wounds or Lesions

CDRMREC reduced the spontaneous pain (without diminution of other sensation) at the site of injury and accelerated healing of surface wounds, lacerations, lesions such as dermal ulcerations, dermatitis, psoriasis, eczema and like conditions. CDRMREC caused rapid epithelialization of those wounds, lacerations and lesions down to the dermal base. The formula has closed lacerations in less than 4 hours. The formula enhanced and accelerated skin surface circulation while stopping bleeding at the wound site within 3 minutes. CDRMREC subsequently diminished scabbing and scarring. The formula rapidly reduced the swelling associated with sprains and bruises. The formula has also rapidly removed the swelling and pain of bee and wasp envenomation.

An example in point is that of a 4 mm diameter by 5 mm deep traumatic avulsion ulcer. Commencing 10 minutes after the wounding, CDRMREC was used to irrigate the lesion constantly over a 7-hour span. Bleeding at the wound site stopped within the initial 2 minutes of CDRMREC usage. During the initial 10 minutes of CDRMREC irrigation, pain was markedly reduced and the ulcer developed rolled edges. The lesion appeared to be filling in with epithelium during the first 3 hours. The ulcer seemed to have completely epithelialized during the first 6 hours of CDRMREC application.

In the case of a 160-square centimeter decubitus stasis ulcer of 16-months duration, CDRMREC application caused complete complete epithelialization in a 4-day time span. The CDRMREC solution was applied 3 times a day and dressed with 2 layers of dry gauze and paper tape.

Hair and Scalp

CDRMREC treated dandruff, stopping its occurrence after the second application. It reduced hair loss and stimulated hair follicles by enhancing surface circulation which aided in restoring follicular viability. There is anecdotal evidence of new hair growth after the tenth week caused by CDRMREC application on a daily basis.

Acne

CDRMREC was used successfully as an adjunct when treating acne. In older skin it improved the tone and restored dermal eleasticity. CDRMREC removed dead dermal cells and controlled or reduced wrinkles. After facial peels it diminished the pain and speeded the recovery.

Hemorrhoids

CDRMREC in the form of a gelatin suppository, restored competence to the affected venous valves in cases of bleeding hemorrhoids while stopping the bleeding within minutes of application. After an average of three doses the hemorrhoids were reported to have disappeared.

Dental

CDRMREC stopped the bleeding and caused the gum to reattach to the tooth surface in several cases of periodontal gum disease.

Animals

CDRMREC treated frost bite in cows by repairing the surface micro-arterials in the teats and udder. It also treated mastitis without antibiotics and teat ulcerations in cows and prevented bacterial infections in injured, lacerated udders which had become contaminated with fecal material.

The following field trials of CDRMREC are descriptive of these results:

CDRMREC was applied topically to a 64-sq. cm suppurating ulcer on the top left hindquarter of a prize Flemish Giant rabbit. Within one hour of application, the ulcer had ceased suppurating and was 75% filled in. The following morning (18 hours later), the ulcer was completely filled in with healthy tissue. In 3 weeks, the area had regenerated its hair and appeared normal.

CDRMREC was applied topically to one badly chapped (bleeding) teat. The chapped teat had been treated with Bag Balm over the preceding 3 days with no visible improvement. After the first application (pre-milking) the bleeding stopped immediately. The teat surface softened sufficiently for successful milking. After the milking, CDRMREC was reapplied to the chapped area and by the following morning, it was reported that the lesion was healed.

CDRMREC was applied topically to 4 chaffed and encrusted teats. The composition was applied to the ends of the 4 encrusted teats after the milking. The following morning, the encrustation was reported to have vanished and the chaffing appeared to be less evident. There was no further application of CDRMREC or any other medication. Later, the chaffed area was reported healed.

CDRMREC was applied topically prior to milking, to a 49-sq. cm. chaffed and bleeding lesion on an udder. The bleeding stopped immediately (less than 2 minutes). The lesion was recoated after the milking was completed. The animals discomfort was evident prior to the first application of CDRMREC. However, following the second application of CDRMREC, the cow showed no signs of discomfort. There were no further applications of CDRMREC. The following morning the lesion was greatly improved and later the lesion was reported healed.

CDRMREC was infused up the teat duct of all 4 quarters of a cow that had clinical mastitis in the left hindquarter. The afflicted quarter had been previously treated with erythromycin one time on the previous day, but the swelling still remained, and that quarter was not giving good milk. Additionally, because of a differential in the vacuum when milking the cow, infected discharge from the left hindquarter contaminated the left fore quarter which then began to show symptoms of clinical mastitis (flaking in the milk). The left fore quarter had not been infused with erythromycin. Following only one infusion of 10 ml per quarter of CDRMREC, it was reported the following morning that all 4 quarters were completely normal. All signs of swelling were gone. The milk from all quarters was normal and untainted.

Treatment with CDRMREC was commenced on a cow that had previously had mastitis in the right hindquarter which resulted in a non-productive quarter. Treatment consisted of six 10 ml intramamery ductal infusions of CDRMREC in the afflicted quarter following each milking. After the sixth treatment an improvement was observed in the quality of the output of the afflicted quarter resulting in a change from a cheesy to a milky consistency.

The following on cows at a local farm, to further demonstrate the effectiveness of the composition of the invention.

A Jersey cow was suffering from mastitis in the right forequarter and had received an antibiotic infusion in that quarter. She had a hard swelling described as the size of a soft ball in the upper part of the quarter. The next day, after the PM milking, she received only one 10 ml infusion of CDRMREC in each of her quarters.

An hour-and-a-half after the infusion, the swelling was observed to be reduced to the size of a tennis ball. On the following morning, the swelling was still present and estimated at golf ball size. Her milk appeared normal. Three days later, the swelling was still present and like a flattened golf ball but the milk tested normal.

Another Jersey cow had a laceration about the size and shape of a half-dollar on the left side of the udder. She also had severe edema of the udder. The laceration was accidental and the edema was the result of recent calving. After the PM milking on the laceration was disinfected. Then 5 ml of CDRMREC was applied to the wound and a tape butterfly was affixed. The entire udder was then treated with 15 ml of CDRMREC which was massaged into the surface. In less than one-half hour, the edema was observed to have reduced by 50%. The following morning the edema had reduced to 85% of its original size. The laceration had softened but the flap had not reattached. At AM milking 4 days later, the flap had still not reattached nor had the edema reduced any further. 3 days later, the flap was cut-off. The underlying lesion filled in with normal tissue within a 2-day period, and the edema had disappeared.

Yet another Jersey cow had severe edema of the udder due to recent calving. After the PM milking, 10 to 15 ml of CDRMREC was massaged into the entire surface of the udder. In less than one-half hour, the edema had reduced by 50%. The next day the edema had reduced to 84% of its original size, and, a week later, the edema disappeared.

While the invention has been described with particular reference to certain embodiments thereof, it will be understood that changes and modifications may be made which are within the skill of the art. Accordingly, it is intended to be bound only by the following claims, which.

What is claimed is:

1. A method of treating wounds, lesions, lacerations, burns and ulcers in humans and animals which comprises administering thereto a composition of the reaction product of arginine and p-aminobenzoic acid.

2. A method according to claim 1 in which said composition includes a solvent.

3. A method according to claim 2 in which said solvent is water.

4. A method according to claim 1 in which said composition is in the form of a powder, solution, gel or emulsion.

5. A method according to claim 1 in which said composition includes, by weight, about 0.5–10% of said reaction product.

6. A method according to claim 1 in which said composition is administered topically.

* * * * *